US006623441B1

United States Patent
Kihara et al.

(10) Patent No.: US 6,623,441 B1
(45) Date of Patent: Sep. 23, 2003

(54) BLOOD-PURIFYING APPARATUS AND ARTIFICIAL KIDNEY USING THE SAME

(76) Inventors: Kazuhiko Kihara, 9-7, Kotsubo 6-chome, Zushi-shi, Kanagawa 249-0008 (JP); Akio Yamada, 9-7, Takiyama 4-chome, Higashikurume-shi, Tokyo 203-0033 (JP)

( * ) Notice: Subject to any disclaimer, the term of this patent is extended or adjusted under 35 U.S.C. 154(b) by 69 days.

(21) Appl. No.: 09/744,808
(22) PCT Filed: Jun. 1, 2000
(86) PCT No.: PCT/JP00/03553
   § 371 (c)(1),
   (2), (4) Date: Apr. 6, 2001
(87) PCT Pub. No.: WO00/72898
   PCT Pub. Date: Dec. 7, 2000

(30) Foreign Application Priority Data

Jun. 1, 1999 (JP) ............................. 11-153574

(51) Int. Cl.[7] ............................. A61M 37/00
(52) U.S. Cl. .................... 604/4.01; 604/5.01; 604/5.02; 604/5.04; 604/6.09
(58) Field of Search ............... 604/4.01, 5.01, 604/5.02, 5.04, 6.09

(56) References Cited

U.S. PATENT DOCUMENTS

| | | | | |
|---|---|---|---|---|
| 3,878,564 A | * | 4/1975 | Yao et al. ................... | 604/5.04 |
| 3,994,799 A | * | 11/1976 | Yao et al. ................... | 604/5.04 |
| 4,212,738 A | * | 7/1980 | Henne ................... | 210/321.75 |
| 4,963,265 A | * | 10/1990 | Okarma et al. ........... | 210/502.1 |
| 5,284,470 A | * | 2/1994 | Beltz ...................... | 210/321.71 |
| 5,549,674 A | * | 8/1996 | Humes et al. ................ | 514/12 |
| 6,193,681 B1 | * | 2/2001 | Davidner et al. ........... | 205/435 |
| 6,200,485 B1 | * | 3/2001 | Kitaevich et al. ........... | 210/134 |

* cited by examiner

Primary Examiner—William C. Doerrler
Assistant Examiner—Filip Zec
(74) Attorney, Agent, or Firm—Pillsbury Winthrop LLP

(57) ABSTRACT

An artificial kidney capable of cleaning blood, like a kidney of a healthy body, by any person even at home which is small in the size and simple in the structure and handling, without requiring any pharmaceutical solution.

A metabolic end product separation chamber (9) is placed to the center of a cylindrical centrifugator (7) for circulating blood continuously and separating it into blood cell ingredients and plasma ingredients for conducting ultrafiltration of the separated plasmas and intaking water, serum electrolytes and unnecessary metabolic end products, in which a water re-absorbing module (11) capable of flowing the concentrated plasma ingredients and re-absorbing the water content and the serum electrolytes to obtain a cleaned plasma ingredient is placed, and the obtained cleaned blood ingredients are mixed with the blood cell ingredients separated by the centrifugator (7) to obtain cleaned blood.

4 Claims, 1 Drawing Sheet

BLOOD-PURIFYING APPARATUS AND ARTIFICIAL KIDNEY USING THE SAME

This application is the national phase of International application PCT/JP00/03553 filed Jun. 1, 2000 which designated the U.S.

TECHNICAL FIELD OF USE

The present invention concerns a blood cleaning apparatus for removing unnecessary metabolic end products such as urea, uric acid and creatinine, thereby cleaning blood, as well as an artificial kidney using the same mechanism.

BACKGROUND ART

An artificial kidney is used as an artificial organ for patients suffering from renal insufficiency whose renal functions for discharging unnecessary metabolic end products in blood as urine are deteriorated or lost, and this is adapted for cleaning patient's blood by separation membranes to substitute the natural renal functions to some extent.

A blood cleaning apparatus is incorporated in the artificial kidney, and the cleaning apparatus is classified into three types, namely, a dialysis type blood cleaning apparatus using dialysis membranes, a filtration type blood cleaning apparatus using ultrafiltration membranes and a plasma separation type blood cleaning apparatus using microfiltration membranes.

The dialysis type blood cleaning apparatus is referred to as a dialyzer in which hollow fibers made of dialysis membranes are disposed, and blood is caused to flow to the inside while a dialysis liquid is caused to flow on the outside of the hollow fibers, so that unnecessary metabolic end products in blood having relatively small molecular weight up to several thousands, such as urea, uric acid and creatinine are discharged outside of the hollow fibers to clean the blood.

The filtration type blood cleaning apparatus has hollow fibers formed of ultrafiltration membranes disposed therein, in which an trans-membrane pressure difference is exerted between the inside and the outside of the hollow fiber, instead of using the dialysis liquid, blood is caused to flow inside the hollow fibers and form a negative pressure at the outside thereby conducting filtration of blood at negative pressure or form a positive pressure in the inside thereby conducting filtration of blood at positive pressure, so that low molecular weight proteins such as β2-microglobrin having molecular weight up to several tens thousands are removed.

Further, the plasma separation type cleaning apparatus is adapted to separate blood into blood cell ingredients and plasma ingredients by a plasma separator equipped with microfiltration membranes, extract the plasma ingredients, discard the plasmas and replace them with clean plasmas.

However, when blood is cleaned by the dialysis type blood cleaning apparatus, dialysis liquid is required by as much as 150 to 200 liters in dialysis 1 trial in order to always exchange the dialysis liquid with the fresh one, to cause a problem of the size of the apparatus which is inevitably increased.

Further, when blood is cleaned by the filtration type blood cleaning apparatus, a supplementary liquid is supplied to veins which return cleaned blood to a body for supplementing filtrates removed from the blood. Since the supplementary liquid is directly mixed to the blood, it should have a composition approximate to that of the plasmas and be kept in a sterile state, which involves a problem of troublesome aspect handling and increased cost compared with blood dialysis.

Further, when the blood is cleaned by the plasma separation type blood cleaning apparatus, a great amount (from 2 to 3 liter) of plasmas is required. In addition, plasma preparations are always lacking in Japan and are extremely expensive, as well as they involve a problem of causing side effects such as hepatitis and allergy as complications.

In addition, when any type of the blood cleaning apparatus is used, since the time required for cleaning blood in a whole body is as long as from about 5 to 6 hours for 1 session, and the blood cleaning operation must be conducted about three times a week, namely, every other day. This constraint in view of time imposes a considerable burden on the quality of life of patients, and greatly restricts patients' social activities.

Further, some pharmaceutical solutions have to be supplied in any of the blood cleaning apparatus. For example, a large amount of dialysis liquid and supplementary liquid are used for dialysis type and filtration type blood cleaning apparatus, or expensive plasma preparations are used in the plasma separation type blood cleaning apparatus. So, monitors for controlling the supply conditions or controllers for regulating the flow rate of them are required, resulted in making the apparatus more complicated and expensive.

On the other hand, a kidney of a healthy body conducts ultrafiltration about 180 liters of blood through about one million of glomerulus per day, and discharges from 1 to 2% of water content together with unnecessary metabolic end products to the outside of a body and absorbs from 98 to 99% of remaining water again together with serum electrolytes. In glomerulus, a filtration amount is 125 cc/min and a discharge amount to the outside of the body is 2 cc/min.

Then, if the function identical to that of the kidney of the healthy body can be reproduced, blood can be cleaned with no requirement for the pharmaceutical liquid at all.

Then, the technical objective of the present invention is to enable cleaning of blood at home during sleeping time, without requiring any pharmaceutical liquid at all, in a small and simple structure in the similar manner as in the kidney of the healthy body.

DISCLOSURE OF THE INVENTION

The present invention concerns a blood cleaning apparatus to be used in an artificial kidney for cleaning blood taken from a body, and circulating it back to the body. It comprises, in a casing equipped with a blood inlet on one side and a blood cell ingredient outlet on the other side, a centrifugator having a rotary cylinder for exerting a centrifugal force on blood to separate them into blood cell ingredients and plasma ingredients. A metabolic end product separation chamber, having a cylindrical ultrafiltration membrane for removing water, serum electrolytes and unnecessary metabolic wastes from the plasma ingredients collected to a portion near the center. Then, a water re-absorbing module comprising hollow fiber dialysis membranes for flowing concentrated plasma ingredients from which water, serum electrolytes and unnecessary metabolic end products have been removed by the cylindrical ultrafiltration membrane and re-absorbing the water, serum electrolytes and unnecessary metabolic end products taken into the separator chamber, substantially in a coaxial arrangement.

The term "blood cell ingredients" used in the present specification mean not only the blood cell ingredients in the strict sense, but mean those mainly comprising blood cell ingredients taken out of the blood. In the same manner, the term "plasma ingredients" not only mean plasma ingredients in the strict sense but mean those mainly comprising plasma ingredients taken out of blood.

According the present invention, blood flown from the blood inlet into the casing flows from one end to the other end thereof and is passed through the inside of the rotary cylinder via a centrifugator and separated centrifugally. In consequence, blood cell ingredients are collected near the outer circumference while the plasma ingredients are collected near the center, and the blood cell ingredients, when reach the other end, are introduced from the blood cell ingredient outlet formed to the casing to the outside.

A metabolic end product separation chamber comprising a cylindrical ultrafiltration membrane is formed at the center of the rotary cylinder and, when a differential pressure of about 100 mmHg is exerted between the inside and the outside of the chamber, unnecessary metabolic end products such as urea, uric acid, creatinine in the plasma ingredients, as well as water content and serum electrolytes are taken into the metabolic end product separation chamber and cleaned, while the plasma ingredients in which serum proteins are concentrated reach the other end of the casing during flow of the plasma ingredients to the other end of the hollow fiber membranes.

When the concentrated plasma ingredients are introduced to the inside of the hollow fiber dialysis membranes of the water re-absorbing module transferred to the metabolic end product separation chamber, water and the serum electrolytes, among water, serum electrolytes and unnecessary metabolic end products taken into the metabolic end product separation chamber, are allowed to permeate into the hollow fiber dialysis membranes and re-absorbed and remained in the metabolic end product separation chamber by the difference of the concentration of serum protein (albumin) between the inside and the outside of the hollow fiber dialysis membranes.

When the plasma ingredients diluted to an ordinary concentration by passing through the water re-absorbing module and blood cell portions taken previously are mixed, cleaned blood can be obtained.

BEST MODE FOR PRACTICING THE INVENTION

Figure 1:
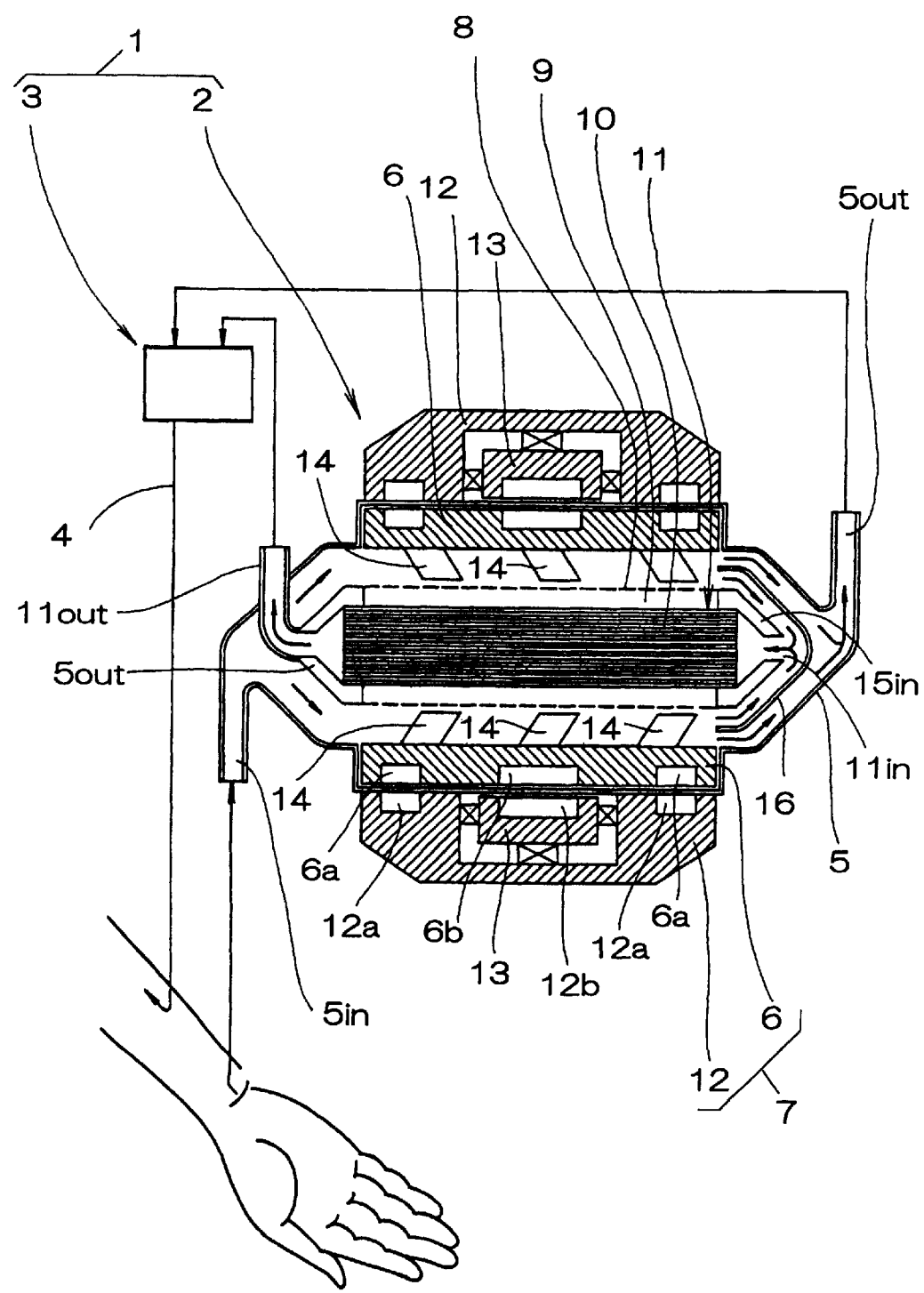
FIG. 1 is an explanatory view showing an artificial kidney according to the present invention.

The mode of practicing the present invention will be explained specifically based on the drawings.

An artificial kidney 1 according to an embodiment of the present invention comprises a blood cleaning apparatus 2 in which blood is caused to flow in, and blood cell ingredients and cleaned plasma ingredients to flow away, and a mixer 3 for mixing the blood cell ingredients and the cleaned plasma ingredients and returning them to a body, which is interposed to an extracorporeal circulatory system 4 for circulating blood taken from a body again to the inside of the body.

The blood cleaning apparatus 2 comprises, in a casing 5 equipped with a blood inlet 5in on one side and an outlet for blood cell ingredients 5out on the other side, a centrifugator 7 equipped with a rotary cylinder 6 for exerting centrifugal force on the blood to separate the blood into blood cell ingredients and plasma ingredients. A metabolic end product separation chamber 9 comprising cylindrical ultrafiltration membrane 8 for up taking water, serum electrolytes and unnecessary metabolic end products from the plasma ingredients are collected to a portion near the center and a water re-absorbing module 11 comprising hollow fiber dialysis membranes 10 for circulating concentrated blood plasma ingredients, with which water, serum electrolytes and unnecessary metabolic end products are transferred through the cylindrical ultrafiltration membranes 8 and then re-absorbing the water and the serum electrolyte by the separation chamber 9.

A driving device 12 is disposed to the outer circumferential surface of the casing 5 for rotationally driving the rotary cylinder 6 of the centrifugator 7 in a magnetically raised state relative to the inner circumferential surface of the casing 5.

The driving device 12 comprises fixed magnets 12a opposed so as to cause repulsion between raising magnets 6a disposed on both right and left ends at the outer circumferential surface of the rotary cylinder 6 and rotational magnets 12b which is disposed being opposed so as to cause attraction force relative to the driving magnets 6b disposed at the center on the outer circumferential surface of the rotary cylinder 6, so that an impeller 13 carrying the rotary magnets 12b is rotationally driven by a predetermined number of rotation.

The rotational cylinder 6 has vanes 14 each formed at a predetermined distance on the inner circumferential surface thereof so as to cause rotating streams of blood flowing between the rotational cylinder 6 and the cylindrical ultrafiltration membranes 8 thereby exerting a centrifugal force.

With such a constitution, the blood cell ingredients in the blood are collected near the outer circumference and the plasma ingredients are collected near the center.

The cylindrical ultrafiltration membrane 8 forming the metabolic end product separation chamber 9 comprises, for example, polyacrylonitrile series membranes sterilized by γ-rays or a cellulose acetate series membrane sterilized by an ethylene oxide gas are formed into a cylindrical shape, which is mounted to spinning cylinders 15in and 15out disposed on both ends of the water re-absorbing module 11.

Then, when a trans-membrane pressure difference of about 100 mmHg is exerted between the inside and the outside of the cylindrical ultrafiltration membrane 8 to form a positive pressure on the outside of the chamber 9, low molecular weight materials of molecular weight up to several tens thousands, for example, unnecessary metabolic end products such as urea, uric acid, creatinine and water permeate through the cylindrical ultrafiltration membrane 8 and are taken into the chamber 9.

With such a constitution, the blood cell ingredients flowing along the outside of the chamber 9 are cleaned and serum proteins are concentrated.

The water re-absorbing module 11 has an inlet 11in opened to the other side of the casing 5 and an outlet 11out led to the outside of the casing 5.

Then, the hollow fiber dialysis membranes 10 are bundled by the number of about 100,000 and both end openings are attached to polymeric or metal spinning 15in and 15out constituting the inlet 11in and the outlet 11out so as to be in communication with the inlet 11in and the outlet 11out.

For the hollow fiber dialysis membrane 10, Cuprophane (trade name of products, manufactured by Enka AG (German)) prepared from dialysis membranes of regenerated cellulose fibers into hollow fibers having an inner diameter of about 300 μm is used for instance.

Since the hollow fiber dialysis membranes 10 are located inside the cylindrical ultrafiltration membrane 8 mounted to the spinning cylinders 15in and 15out, they are placed through the metabolic end product separation chamber 9, and the outside of the hollow fiber dialysis membranes 10 is filled with water containing unnecessary metabolic end products taken into the metabolic end product separation chamber 9.

In this case, each of the hollow fiber membranes 10 is potted only on both ends secured to the spinning cylinders 15in and 15out, but not potted at the central portion, so that water flows along the surface of each of the hollow fiber dialysis membranes 10.

A cap-shaped concentrated plasma introduction guide 16 is placed on the other end of the casing at a position opposed to the flow of the concentrated plasma ingredients collected near the center of the rotational cylinder 6 for introducing the flow to the center, reversing the direction and introducing the flow to the inlet 11in of the water re-absorbing module 11.

With such a constitution, water and serum electrolytes already transferred into the metabolic end product separation chamber 9 are re-absorbed during flow of the concentrated plasma ingredients in the hollow fiber dialysis membranes 10.

The blood cell ingredient outlet 5out formed to the casing 5 and the outlet 11 of the water re-absorbing module 11 are connected to the mixer 3, and they are mixed and returned to the inside of the body through the extracorporeal system 4.

An example of the constitution of the present invention is as has been described above, and the operation will be explained next.

Explanation will be made to a case of taking out 150 cc/min of blood from a body, taking it into the blood cleaning apparatus 2 of the artificial kidney 1 through the extracorporeal recycling system 4, separating the same into 110 cc/min of blood cell ingredients and 40 cc/min of plasma ingredients by the centrifugator 7, taking 20 to 36 cc/min of water, serum electrolytes and unnecessary metabolic end products from the plasma ingredients to the metabolic end product separation chamber 9 to concentrate the albumin in the blood by 5 to 10 times, introducing 20 to 4 cc/min of obtained concentrated plasma ingredients to the water re-absorbing module 11, re-absorbing water in an amount substantially identical with that of the removed water together with serum electrolytes.

A blood hematocrit value of a patient suffering from chronic renal insufficiency is usually kept at 25 to 30% and, when it is supplied to the centrifugator 7, 110 cc/min of blood cell contents are collected near the outer circumference of the rotary cylinder. It will be concentrated to a hematocrit value of about 40%, and supplied from the blood cell ingredient outlet 5out to the mixer 3.

Further, 40 cc/min of plasma ingredients are collected near the center of the rotary cylinder 6 and flow along the cylindrical ultrafiltration membrane 8 of the metabolic end product separation chamber 9.

In this case, unnecessary metabolic end products such as urea, uric acid and creatinine, as well as water and serum electrolytes in the plasma ingredients are transferred into and cleaned in the metabolic end product separation chamber 9 together with about 20 to 36 cc/min of water, and 20 to 4 cc of plasma ingredients in which the serum proteins are concentrated reach the other side of the casing.

The water-removing performance of ultrafiltration membranes commercially available at present is about 100 cc/mmHg·hr·m² and, when trans-membrane pressure of 100 mmHg is exerted between the inside and the outside of the metabolic end product separation chamber 9 to concentrate albumin by about 10 times (removing 36 cc of water content), the effective membrane area $S_1$ of the cylindrical ultrafiltration membrane 8 is:

$S1 \approx 0.2$ m² according to: $36=100\times100\times S_1/60$, and it may suffice to use a cylindrical ultrafiltration membrane 8, for example, having a radius of 10 cm and a length of about 30 cm.

In addition, as described later, water is absorbed by utilizing a difference of albumin concentration in the water re-absorbing module 11 and, in this case, it is considered that the albumin concentration rate of about 5 times may suffice.

However, when albumin is concentrated, protein cakes are formed on the surface of the cylindrical ultrafiltration membranes 8 to lower the water removing effect, and it is preferred to adopt an area of about 0.2 m².

With such a constitution, referring to the plasma ingredients, the albumin as the serum proteins thereof is concentrated by about 5 to 10 times and introduced in the hollow fiber dialysis membranes 10 of the water content reabsorbing module 11 via concentrated plasma introducing guide vane 16.

When the hollow fiber dialysis membranes 10 absorb water at about normal albumin concentration (4 g/dl) in blood, they have a water absorbability equivalent with the intermembrane pressure difference of about 25 mmHg as an osmotic pressure of colloid, but it is considered to have a water absorbability equivalent with the inter-membrane pressure difference of about 125 mmHg assuming the albumin is concentrated to about five times the usual value (20 g/dl) (about 250 mmHg at 10 times) Since the performance of the ultrafiltration membrane of the hollow fiber dialysis membranes 10 is about 2 cc/mmHg·hr·m², in a case of absorbing water at 36 cc/min only based on the concentration difference of albumin, it may suffice that the effective film area $S_2$ of the hollow fiber dialysis membrane 10 is:

$: S_2 \approx 0.13$ m² according to: $36=2\times126\times S_2/60$.

Assuming the use of the hollow fiber membranes 10 prepared by bundling 10,000 fibers each having an inner diameter of 300 μm and a length of 30 cm, it may suffice that the effective membrane $S_2'$ is:

$S_2'=7\times0.03\times30\times10,000 =2.8$ m².

Since the hollow fiber dialysis membranes 10 have a small sieving coefficient for small molecular weight materials such as urea, uric acid and creatinine, when the concentrated plasma ingredients are flown into the hollow fiber dialysis membranes 10, among water, unnecessary metabolic end products and serum electrolytes, only the water and the serum electrolytes permeate through the hollow fiber dialysis membranes 10 and are re-absorbed, so that the albumin concentration in the concentrated plasma ingredients is diluted to the initial concentration.

Further, since unnecessary metabolic end products such as urea, uric acid and creatinine are remained in the metabolic end product separation chamber 9, the metabolic end product separation chamber 9 formed integrally with the water re-absorbing module 11 is preferably designed to be disposable.

With such a constitution, cleaned plasma ingredients are delivered at the rate of 40 cc/min from the outlet 11out of the water re-absorbing module 11 to the mixer 3, and mixed with 110 cc of blood cell ingredients delivered from the blood cell ingredient outlet 5out, so that 150 cc/min of blood is cleaned and returned to the body by way of the extracorporeal system 4.

As described above, since the artificial kidney 1 of this embodiment removes only the unnecessary metabolic end products such as urea, uric acid and creatinine contained in the blood, and re-absorbs most of water and serum electrolytes in the same manner as the healthy body kidney, pharmaceutical solution such as dialysis liquid, supplementary liquid and serum preparation are no more necessary at all and, accordingly, a monitor for determining the supply conditions and a controller for controlling the flow rate are no more necessary, and the apparatus can be reduced in the size and simplified in the structure.

In addition, since troublesome handling for pharmaceutical solution is no more necessary and the operation for the apparatus itself is simple, patients suffering from renal insufficiency, who can not clean blood by dialysis unless they go to special hospitals, can now clean the blood while they are sleeping at home or even during travel.

Explanations have been made to the case of coaxially arranging the rotary cylinder 6 of the centrifugal separator 7, the metabolic end product separation chamber 9 formed by the cylindrical ultrafiltration membranes 8 and the water re-absorbing module 11 formed by the hollow fiber dialysis membranes 10 in the foregoing explanations, the coaxial arrangement may be to such an extent that the metabolic end product separation chamber 9 is formed in the centrifugal separator 7 and the water re-absorbing module 11 is disposed further in the inside thereof providing that this cause no trouble for the cleaning of blood.

INDUSTRIAL APPLICABILITY

As described above, since the artificial kidney according to the present invention can clean blood without requiring no pharmaceutical solution at all in the same manner as the kidney of the healthy body, and blood can be cleaned while utilizing sleeping period both at home and during travel, patients can be free from constraint in view of time for carrying out cleaning of blood through dialysis, and it is extremely useful as a portable and convenient artificial kidney.

What is claimed is:

1. A blood cleaning apparatus to be used in an artificial kidney for cleaning blood taken from a body, and circulating it to the body, which comprises
    a casing having a blood inlet on one side and a blood cell ingredient outlet on the other side thereof,
    a centrifugator within the casing, having a rotary cylinder for exerting a centrifugal force on blood to separate the same into blood cell ingredients and plasma ingredients, a metabolic end product separation chamber having a cylindrical ultrafiltration membrane for intaking water, serum electrolytes and unnecessary metabolic end products from the plasma ingredients collected to a portion near the center, and a water re-absorbing module comprising hollow fiber dialysis membranes for flowing concentrated plasma ingredients from which water, serum electrolytes and unnecessary metabolic end products have been removed by the cylindrical ultrafiltration membrane, and re-absorbing the water, substantially in a coaxial arrangement.

2. A blood cleaning apparatus as defined in claim 1, wherein the water re-absorbing module is placed passing through the metabolic end product separation chamber, and the inlet is opened toward the other end of the casing and the outlet is led to the outside of the casing, and
    a concentrated plasma introduction guide vane is disposed to the other end of the casing at a position opposed to the flow of the concentrated plasma ingredients collected near the center of the centrifugator for reversing the flow and introducing it to the inlet of the water re-absorbing module.

3. A blood cleaning apparatus as defined in claim 1 or 2, further comprising a driving device for rotating the rotary cylinder of the centrifugator without physical contact by a rotary magnet disposed outside of the casing.

4. An artificial kidney for cleaning blood taken from a body and circulating the same to the body, which includes:
    a blood cleaning apparatus for causing the blood to inflow and taking out blood cell ingredients and cleaned plasma ingredients, and a mixer for mixing the blood cell ingredients and the cleaned plasma ingredients and returning them to the body, wherein
    the blood cleaning apparatus comprises: a casing having a blood inlet on one side and a blood cell ingredient outlet on the other side thereof,
    a centrifugator within the casing having a rotary cylinder for exerting a centrifugal force on blood to separate the blood into blood cell ingredients and plasma ingredients, a metabolic end product separation chamber having a cylindrical ultrafiltration membrane for intaking water, serum electrolytes and unnecessary metabolic end products from the plasma ingredients collected to a portion near the center, and a water re-absorbing module comprising hollow fiber dialysis membranes for flowing concentrated plasma ingredients from which water, serum electrolytes and unnecessary metabolic end products had been removed by the cylindrical ultrafiltration membrane and then re-absorbing the water, substantially in a coaxial arrangement.

* * * * *